United States Patent
Kamrukov et al.

(10) Patent No.: US 6,264,802 B1
(45) Date of Patent: Jul. 24, 2001

(54) METHOD AND DEVICE FOR UV TREATMENT OF LIQUIDS, AIR AND SURFACES

(75) Inventors: Alexandr Semenovich Kamrukov, ul. Kotsubinskogo 7-2-15, 121355 Moscow; Sergei Gennadievich Shashkovsky, ul. Krzhizhanovskogo 32-37, 117259 Moscow; Mikhail Stepanovich Yalovik, Moscow; Evgeny Dmitrievich Korop, Troitsk; Vladimir Pavlovich Arkhipov, Moscow; Nikolai Pavlovich Kozlov, Moscow; Valery Anatolievich Kukanov, Moscow, all of (RU)

(73) Assignees: Alexandr Semenovich Kamrukov; Sergei Gennadievich Shashkovsky; Mikail Sepanovich Yalovik, all of Moscow (RU); Vladimirovich Soloviev, Paris (FR)

(*) Notice: Subject to any disclaimer, the term of this patent is extended or adjusted under 35 U.S.C. 154(b) by 0 days.

(21) Appl. No.: 09/242,415
(22) PCT Filed: Jun. 23, 1997
(86) PCT No.: PCT/RU97/00195
§ 371 Date: Feb. 16, 1999
§ 102(e) Date: Feb. 16, 1999
(87) PCT Pub. No.: WO98/42624
PCT Pub. Date: Oct. 1, 1998

(51) Int. Cl.$^7$ ............... C07C 1/00; B01D 53/00; B01D 17/06
(52) U.S. Cl. ............... 204/158.2; 204/157.15; 204/157.3; 210/748
(58) Field of Search ............... 204/157.15, 157.3, 204/158.2; 210/748

(56) References Cited

U.S. PATENT DOCUMENTS

| | | | |
|---|---|---|---|
| 4,366,125 | 12/1982 | Kodera et al. | 422/295 |
| 5,130,031 | 7/1992 | Johnston et al. | 210/748 |

FOREIGN PATENT DOCUMENTS

| | | |
|---|---|---|
| 3843679 | 7/1990 | (DE) . |
| 0701972 | 3/1996 | (EP) . |
| 701972 * | 3/1996 | (EP) . |
| 2001629 | 10/1993 | (RU) . |
| 2001882 * | 10/1993 | (RU) . |
| 2008042 | 2/1994 | (RU) . |
| 2031659 | 3/1995 | (RU) . |
| 2031850 | 3/1995 | (RU) . |
| 2031851 | 3/1995 | (RU) . |

* cited by examiner

Primary Examiner—Edna Wong
(74) Attorney, Agent, or Firm—Greer, Burns & Crain, Ltd.

(57) ABSTRACT

A method of treatment of liquid, air and surfaces using UV radiation with a pulse duration of $10^{-6}$ to $10^{-3}$ sec. and a radiation intensity of at least 100 kWt/m$^2$, using a plasma radiation source with a pulsed storage element, wherein the energy stored in the storage element at the time of discharge, the pulse duration and the area of the radiating surface of the radiation source are interrelated as follows: $W_0/A S_{rad} t_{1/2} > 1$, where $W_0$, is the energy stored in the storage element, Joules; $S_{rad}$ is the area of the radiating surface of the radiation source, m$^2$; $t_{1/2}$ is the radiation pulse duration at mid-height of a peak, sec.; $A=10^8$ Wt/m$^2$ is the constant coefficient. A device for the UV treatment of liquid, air and surfaces includes a secondary winding integrated in a series with a charged condenser, and a pulsed lamp to form a discharging circuit.

3 Claims, 1 Drawing Sheet

METHOD AND DEVICE FOR UV TREATMENT OF LIQUIDS, AIR AND SURFACES

This is a national stage application of PCT/RU97/00195 filed Jun. 23, 1997.

FIELD OF ENGINEERING

The present invention relates to the technology of disinfection and purification of fluid media and surfaces and may be used for express air disinfection in rooms, for purification of drinking water and sewages from organic and bacterial impurities as well as for disinfection and sterilization of surfaces including man and animal skin.

BACKGROUND OF THE INVENTION

The method of treatment of open surfaces, liquid and air through the use of UV radiation of continuous spectrum (patent RU 2001629, 1993) is known. In this case sources of impulse UV radiation with impulse duration no more than $5 \times 10^{-4}$ sec. are used, they produce radiation intensity no less than 100 Kw/m$^2$ in treatment area. Bactericidal effect for different microorganisms is achieved in one or several impulses according to integrated energy of radiation dose.

Method of sewage purification from organic substances through use of UV radiation with similar features (patent RU 2001881, 1993 and RU 2031851, 1995) are known. In the latter case UV treatment is combined with use of oxidants.

The devices used in these methods contain an impulse gas discharge lamp, a power supply and control unit with a condenser, a generator of ignitor impulses and an impulse transformer the secondary winding of which is connected in series with the storage condenser and the impulse lamp, thereby providing a discharge circuit (patent RU 2008042, 1994, RU 2031659, 1994 and RU 203 1850, 1994).

The known methods and devices are deficient in efficiency and reliability. The word efficiency as applied to the devices for air disinfection and deodorization designates herein a degree of disinfection or purification of air in a room of predetermined volume which is achieved with a certain consumption of electric energy. In this manner a rise in the efficiency of a unit can be the result of an increase in the bactericidal flow of the UV radiation or of a decrease in the power requirements with all other parameters remaining unchanged.

A severe loss occurs in the transformation of supply line energy into energy of bactericidal UV radiation for the following reasons:

1. During loading of the storage condenser from a direct current source, there occurs a considerable energy loss due to excessively high currents in an early period of the loading process. In addition, elements of the electrical circuit of the unit operated at heavy current lack reliability under intensive operation conditions.
2. For disinfection of air in rooms of a great volume (of the order of 100 m$^3$ and more) significant power (of the order of 1 kW and more) is delivered to the impulse gas-discharge lamp, which requires effective cooling of the lamp and limitation on the ozone-constituting part of the radiation spectrum. That is to say, the lamp needs to be interposed in a liquid coolant (distilled water) and inductive coupling of the ignitor generator with the discharge circuit is possible only in the form of a transformer because mounting of a special ignitor electrode in a liquid at a high delivered voltage is unavailable.
3. During a change-over from preliminary low-power high-voltage break-down to ground discharge impulse, energy losses occur in association with the fact that in order to produce a high temperature in a radiating plasma the inductance L of the discharge circuit must be lowered (for increasing the maximal current) whereas for reliable generation of the ground discharge impulse the inductance must be increased (for increasing the duration of the ignitor impulse to 1 microsec.) The solution to the problem was one compromise. Because of this, on the one hand the plasma temperature fell below optimum magnitudes, resulting in deficient bactericidal UV radiation and inadequate efficiency of the unit. On the other hand, the discharge becomes unstable in early period thereof, due to inevitable fluctuations and spreads of parameters of the lamp and the plasma. This leads to failure and lack of radiation impulses, that is to say to unreliable and unstable operation of the unit.

SUMMARY OF THE INVENTION

The object of the present invention is to increase the efficiency and reliability of UV treatment and of the devices for implementation thereof.

To this end a treatment of liquid, air and surfaces is conducted by UV radiation of continuous spectrum with impulse duration $10^{-6}$–$10^{-3}$ sec. and radiation intensity no less than 100 Kw/m$^2$ using a plasma source of radiation with impulse energy storage under the following relation between parameters of the process:

$$\frac{W_o}{A \times S_{rad} \times t_{\frac{1}{2}}} > 1 \tag{1}$$

Where:

$W_o$ – is the energy stored up in storage at moment of discharge, J;

$S_{rad}$ – is the surface area of the radiating surface of the radiation source, m$^2$;

$t_{\frac{1}{2}}$ – is the duration of a radiation impulse at half-altitude of a peak, sec.;

$A = 10^8 \ W/m^2$ – is a constant coefficient.

The given relation was determined experimentally and it is necessary that the emission spectrum of plasma appears to be predominantly continuous, and that fraction and intensity of radiation pertaining to the UV region are sufficient for effective inactivation of microorganisms and destruction of toxic organic substances.

Treatment of a liquid medium, particularly high-fouled, may be conducted in the presence of an oxidant and/or a photocatalyst. Ozone and hydrogen peroxide are the most acceptable oxidants and titanium dioxide is usable as a photocatalyst, it may be deposited on gauze from stainless steel.

In a preferential variant, an impulse gas-discharge lamp is used as plasma source of radiation and a storage condenser (an electric condenser or a battery of condensers) is used as an impulse energy storage.

Other types of indicated units are allowable. For example, an open high-current gas- and vacuum-discharge or surface high-current discharge (e.g. discharges over surfaces of carbon ceramic, ferrite and so on) are usable as sources of plasma. Inductive storage (inductive coil), flywheel energy storage (e.g. a rotatable rotor) or chemical energy source (e.g. a blasting charge) are useful as impulse storage.

In the proposed device an electric circuit for power supply and control of UV radiation is used.

The device contains an impulse gas-discharge lamp, a power supply and a control unit, equipped with a high-voltage direct current source and a storage condenser, a generator of ignitor impulses and an impulse transformer on ferrite core (for example ring-shaped). The high-voltage d.c. source can be implemented in the form of a high-voltage rectifier and high-voltage coil. A primary winding of the impulse transformer is connected to output of the ignitor generator. A secondary winding is connected in series with the storage condenser and the impulse lamp to form a discharge circuit, parameters of which are bound together by the relation:

$$0,05 < \frac{U^2}{B \times d \times h} \sqrt{C/L_0} < 1 \qquad (2)$$

where:

$U$ – is the voltage of the impulse energy storage, $V$;

$C$ – is the capacitance of the impulse energy storage, $F$;

$L_0$ – is the initial inductance of the discharge circuit, $H$;

$d$ – is the inner diameter of the gas-discharge lamp, $m$;

$h$ – is the separation between electrodes of the plasma source of radiation, $m$;

$B - 10^9 \ W/m^2$ – is the constant coefficient.

Additional and ancillary units required for purposes of providing appropriate devices may be incorporated into particular device constructions but with obligatory use of the mentioned electrical circuit for power supply and control of UV radiation source.

Thus, devices for disinfection of drinking water or for purification of sewages can be provided with a tight flow reactor having inlet and outlet connections, the gas-discharge lamp being accommodated within this reactor.

It is desirable to provide a device for treatment of dermatological diseases and burn wounds incorporating a gas-discharge lamp with a reflector and light filter.

A device for air disinfection and air deodorization in rooms will perform a treatment faster, if it is completed with a fan.

Figure 1:
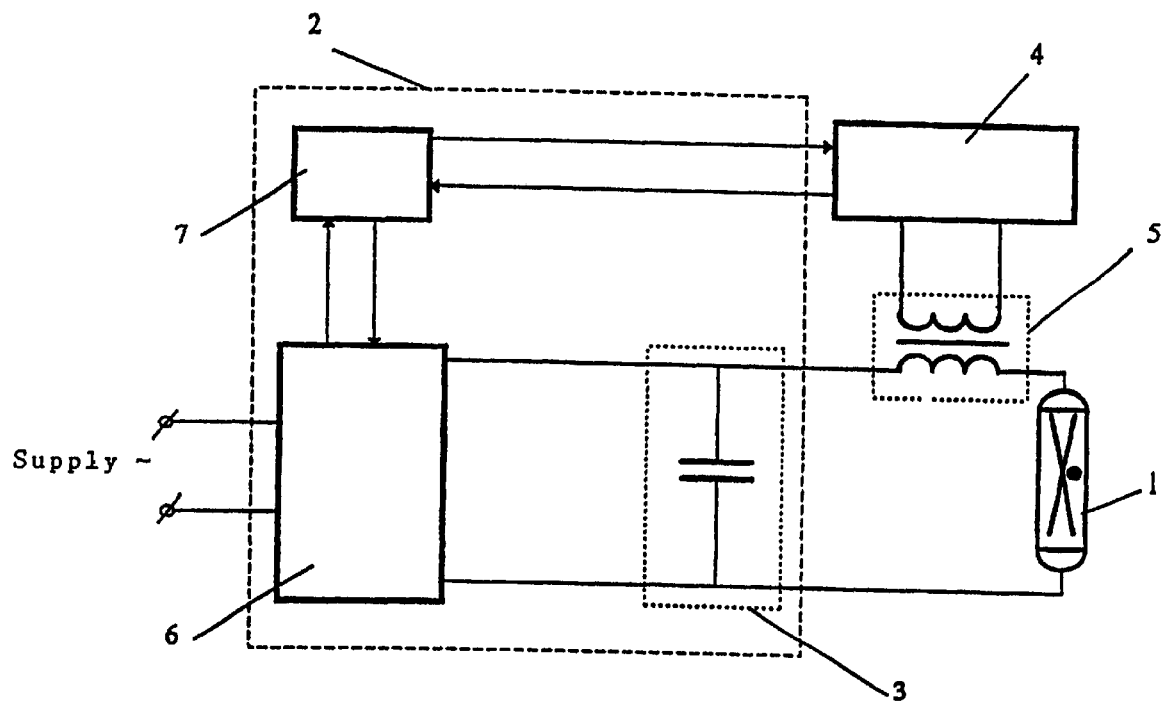
FIG. 1 gives a conceptual diagram of a device for treatment of liquid, air and surfaces with UV radiation. The device contains an impulse gas-discharge lamp 1, a power supply and control unit 2 having a storage condenser 3, a generator of ignitor impulses 4, and an impulse transformer 5. The secondary winding of the latter is connected in series with the storage condenser 3 and the impulse lamp 1 to form the discharge circuit. The supply and control unit 2 is furthermore provided with a high-voltage direct current source 6. The impulse transformer 5 is made on a ferrite core.

A control unit 7 is incorporated into the power supply and control unit 2.

DESCRIPTION OF THE PREFERRED EMBODIMENTS

As an example, experimental data in support of relation (1) are exhibited in the table 1.

TABLE 1

| $W_0/AS_{rad} \ t_{1/2}$ | $T_1$, sec | $T_2$, min | $T_3$, min |
|---|---|---|---|
| 0, 5 | 240 | 32 | 27 |
| 1 | 30 | 4, 0 | 3, 5 |
| 2 | 10 | 2, 1 | 1, 4 |
| 10 | 1, 5 | 0, 2 | 0, 15 |

In the table:
$T_1$ - is the duration of UV treatment for dividing by $10^4$ the level of initial contamination by bacteria $E.\ coli$ (Co = $10^6$ CFU/cm$^2$)
$T_2$ - is the duration of UV treatment of water contaminated by chlorphenol for dividing by 10 the initial contamination index (Co = 1, 5 mg/l)
$T_3$ - is the duration of treatment of water contamined by crude oil (Co = 12 mg/l) with UV radiation in the presence of oxidant (hydrogen peroxide) for dividing by 10 the contamination index.

As may be seen from the exhibited data, the efficiency of UV treatment, both with and without the presence of an oxidant, which efficiency is characterized by the procedure duration (all other factors being equal) is considerably increased by $W_0/ASradt_{1/2} > 1$, suggesting that the spectrum of plasma radiation is continuous and the required level of influence intensity is obtained.

Furthermore, the method of UV treatment is described by an example of device for air disinfection in rooms. As a radiation source, there is used an impulse gas-discharge lamp, the bulb of which is filled with an inert gas, e.g. xenon, at a near-atmospheric pressure (300–700 mm of mercury column).

The gas discharge lamp may be placed in a quartz tube the inner space of which is filled with water for cooling and suppressing the ozone-forming part of the UV radiation spectrum (with wave length less than 210 nm).

The device for air disinfection is located in the neighborhood of the center of a treated room. A necessary operating mode depends on the room dimensions, and is prescribed by control unit 7 and defined by a count of the radiation impulses. An operator starts up the operating mode and thereupon escapes from the room.

After a necessary delay (20–40 sec), the control unit 7 brings into operation the high-voltage dc source 6 and charging of the storage condenser 3 begins. The voltage across the condenser 3 is operated from control unit 7 for which purpose it has a voltage divider, comparator and reference voltage source (they are omitted in FIG. 1). Control unit 7 disconnects the high-voltage dc source 6 and conducts a control impulse to the generator if ignitor impulses 4 when the voltage across the storage condenser 3 reaches a prescribed magnitude (commonly 1–2 kV). Generator if ignitor impulses 4 generates an ignitor impulse with an amplitude of 1–2 kV and a duration of 0.1–1 microsec., inducing a current in the primary winding of the impulse transformer 5. An impulse of amplitude 20–40 kV is consequently formed in the secondary winding of the transformer 5. Because of the electrical connection of the storage condenser 3 with the secondary winding of the transfer 5 and the lamp 1, this voltage is applied to the electrodes of the lamp 1. In lamp 1 filled with inert gas causes a break-down across the electrodes in the form of a conducting channel of weakly ionized plasma. The storage condenser 3 discharges through lamp 1 whereby a powerful impulse of the discharge current causes high-rate heating and ionization of the gas. The resulting plasma heavily radiates with a wide range of spectrum and especially in the UV part. The radiation propagates in all directions through the quartz bulb of the lamp 1, a layer of the distilled water and quartz tube, performing deactivation of bacteria and air pathogen microflora.

Coincidently therewith, a deodorization of air occurs. The deodorization results through destructive photochemical decomposition of the organic molecules of odorant substances.

As the storage condenser 3 finishes the discharging, the plasma of inert gas in lamp cools down, the gas recovers atomic state, the radiation is terminated. The circuit comes to initial state.

Thereupon the process is repeated: control circuit switches on the dc source, the storage condenser is charged to prescribed voltage, the ignitor impulse is generated and so on.

The most high-rate action on air is achieved at radius of 1–2 m from the lamp. To obtain a circulation and an input of the air in the most effectively treated zone treatment, a fan may be used.

As soon as the amount of impulses which had been predetermined by the operator has been generated, the control unit disconnects the device and a treated room is suitable for its direct purpose at once.

The experiment research made with a prototype of the device in a room having a volume of 60 $m^3$ under an artificial air contamination with *Staphylococcus aurens* within the confines of 20,000–42,000 micro bodies per $m^3$ showed that the efficiency of the decontamination reaches 99.99% just within 2 minutes of operation.

Coincidentally with an increase in efficiency, an increase of the device reliability is reached as a result of an absence of omitted impulses and of stability of the impulse parameters.

The efficiency of air deodorization in a room by application of the proposed device has been examined on vapors of a strongly smelling substance, the acetone. The air treatment within 2 minutes reduced the content of the acetone to an amount under 0.1 $mg/m^3$ while the initial content was in the range of 0.73–1.1 $mg/m^3$.

In use of the device for treatment of skin deseases, a medical effect can be modified with the help of a disposable filter having and appropriate transparent domain. As one example, a radiation over a range of wavelenths from 200 to 280 nm has marked bactericid action. The radiation in the range between 280 and 400 nm is tonic and has a therapeutic effect by definite doses. The radiation in the visible range of spectrum (380–780 nm) by suitable doses serves to growth and regeneration of substances.

The comparison data on purification of the sewages from dissolved phenol through the use of UV radiation from the proposed device with a tubular xenon impulse lamp of the "JFP-800" type and titanium dioxide as a catalyst are given in table 2.

TABLE 2

| Operation mode | Initial concentration (Co). mg/l | Radiation intensity $MW/m^2$ | $TiO_2$ | Radiation time, min | Final concentration (Cf), mg/l | Degree of purification Co/cf |
|---|---|---|---|---|---|---|
| 1 | 2, 47 | 0 | + | 10 | 1, 72 | 1, 44 |
| 2 | 2, 47 | 15 | − | 10 | 0, 083 | 29, 8 |
| 3 | 2, 47 | 15 | + | 10 | 0, 002 | 1235 |

The proposed device exhibits the greater efficiency at the same energy expenditure and the greater operation reliability. These advantages result from following factors.

As pointed out above, there is a need to increase a duration of the ignitor impulse, incoming to lamp, from 0.1–0.3 microsec. to 1 microsec. for reduction of energy loss by forming a ground discharge (discharge of the storage condenser through the lamp). This may be achieved by suitable increase of inductance of the discharge circuit. At the same time, it is necessary to reduce the duration of the ground discharge to 100–300 microsec. by retention of the amount of energy stored in the condenser to ensure a high temperature and a reasonable optical density. This leads to diminution of the inductance of the discharge circuit. These opposite requirements will be satisfied by manufacturing the impulse transformer on a ferrite core and fulfilling relation (2).

The own inductance of the second winding of the impulse transformer represents no more than 10 micro H in the absence of a ferrite core. In the ignition process when a high-voltage impulse of the piercing voltage is formed in the discharge circuit, the inductance of active winding of the transformer increases by $\mu$ time ($\mu$ is the relative magnet permeability of ferrite) through influence of the ferrite core.

The work of core correlates with not great current (about 1 A) in the process of ignition. For ferrite of type M 2 000 MH, $\mu$ is about 2000 that is to say, effective inductance magnitude of discharge circuit comprises about 20 mH by primary (preliminary) break-down of the lamp. This magnitude is quite sufficient for increasing the duration of the ignitor impulse to 5–10 microsec. and therefore for loss reduction by forming of a ground discharge impulse.

The magnitude of current in discharge circuit reaches several kA in the process of ground discharge. The magnet permeability of ferrite by these magnitudes of magnetization reduces to $\mu=1$ and the effective magnitude of secondary winding of the transformer comes close to its minimum static (that is to say free of core) magnitude. In such a manner, the inductance of the discharge circuit is minimum during the ground discharge process and optimal conditions for forming of an optically dense, high-temperature plasma severely radiating in the UV range of spectrum are achieved.

Research disclosed that the specific interrelation of parameters of the discharge circuit as defined and covered by relation (2), is a condition of saturation of ferrite core of an impulse transformer and a condition for reducing therethrough the losses by forming a ground discharge impulse.

Simultaneously, a top boundary of the relation (2) defines entering of working point of the core into area of ground discharge, a low boundary may be reached by real magnitudes of inductances of carried conductors, storage condenser and other components only with reduction of the voltage or the capacitance of the storage condenser and that may be reached only with lowering of the energy conducted to the lamp and therefore with reduction of the temperature and optical density of the plasma.

In such a manner the performance of the impulse transformer on ferrite core with regard to relation (2) ensures nonlinear character of the transformer inductance: inductance of discharge circuit during preliminary ignitor impulse differs markedly from it during the ground discharge. This provides optimal combination of parameters in all stages of operation. And the use of a high-voltage current source in the power supply and control unit ensures invariability of the charging current and thereby reduces energy losses by charging of the storage condenser and increases reliability of operation of the electric unit elements.

What is claimed is:

1. A method of treatment of liquids, air and surfaces through the use of UV radiation with continuous spectrum, said method including the step of applying the UV radiation to at least one of the liquids, air or surfaces at an impulse duration of $10^{-6}$–$10^{-3}$ sec. and an intensity of irradiation no less than 100 kW/m$^2$, said radiation being emitted by a plasma source of radiation with impulse energy storage, wherein energy stored up at a moment of discharge the radiation impulse duration and an area of radiating surface of radiation source are bound together by the relation:

$$\frac{W_0}{A \times S_{rad} \times t_{1/2}} > 1$$

where:

$W_0$—is the energy stored up at a moment of discharge, J;

$S_{rad}$—is the radiation surface area of the radiation source, m$^2$;

$t_{1/2}$—is the duration of radiation impulse at half-altitude of a peak, sec;

$A=10^8$ W/m$^2$—is a constant coefficient.

2. The method of claim 1 wherein the treatment by UV radiation is achieved in the presence of an oxidant and/or photocatalyst.

3. The method of claim 2 wherein ozone or hydrogen peroxide is used as the oxidant and titanium dioxide is used as the photocatalyst.

* * * * *